United States Patent [19]

Glenn

[11] 4,227,417
[45] Oct. 14, 1980

[54] DYNAMIC FOCUSING APPARATUS AND METHOD

[75] Inventor: William E. Glenn, Ft. Lauderdale, Fla.

[73] Assignee: New York Institute of Technology, Old Westbury, N.Y.

[21] Appl. No.: 806,005

[22] Filed: Jun. 13, 1977

[51] Int. Cl.² .......................................... G01N 29/00
[52] U.S. Cl. ...................................... 73/625; 128/660
[58] Field of Search .......... 128/2 V, 2.05 Z, 660–661; 73/602, 609, 628, 620–626; 340/1 R, 1 C, 5 H, 5 M, 5 P; 235/92 PS, 92 P; 328/37, 55, 155; 307/221 R, 221 D, 293; 367/11, 122–125

[56] References Cited

U.S. PATENT DOCUMENTS

| 3,403,247 | 9/1968 | Morgan et al. | 364/578 |
|---|---|---|---|
| 3,918,024 | 11/1975 | Macovski | 340/1 R |
| 3,919,683 | 5/1974 | Itamura et al. | 73/626 |
| 4,011,750 | 3/1977 | Robinson | 73/628 X |
| 4,019,169 | 4/1977 | Takamizawa | 340/1 R |
| 4,023,175 | 5/1977 | Brown et al. | 340/1 R X |
| 4,058,001 | 11/1977 | Waxman | 128/2 V X |
| 4,058,003 | 11/1977 | Macovski | 73/609 |
| 4,091,342 | 5/1978 | Whitten | 307/293 X |
| 4,137,007 | 10/1979 | McKeighen et al. | 73/625 |
| 4,152,678 | 5/1979 | Shott et al. | 73/619 |

OTHER PUBLICATIONS

Baker, W. D. et al., "CCD Applications," *Naval Research Reviews*, Dec. 1974, pp. 22–45.
Bernardi, R. B. et al., "A Dynamically Focussed Amsuler Array," 1976 IEEE Symp. Proc., (IEEE Cat #76 CH1120-5SU) Annapolis, Md. 9/28–10/1/76, pp. 157–159.
Ueda, M. et al., "Dynamic Focussing Ultrasonic Transducers Using Analog Switch Phase Shifters," Elec. & Comm. in Japan, vol. 58-A, No. 12, 1975.
Ito, K. et al., "Quantitative Color Ultrasonography, Computer-Aided Simultaneous Tomogram Method", 2d World Congress on UTS in Medicine, Rotterdam, Netherlands, 4–8 Jun., 1973, pp. 364–372.
Malen, R. D. et al., "CCD Dynamically Focussed Lenses for UTS Imaging Systems," Proc. of Intnl. Conf. on Appl. of CCD Devices, 3rd, San Diego, Cal.,1975, pp. 165–171.
Shott, J. et al., "The Razorback CCD: A High Performance Parallel Input Delay Line Architecture," IEEE Intal. Sol. St. Circuits Conference, Feb. 1975, pp. 150–151, 227.

*Primary Examiner*—Kyle L. Howell
*Assistant Examiner*—Francis J. Jaworski
*Attorney, Agent, or Firm*—Martin Novack

[57] ABSTRACT

The disclosure is directed to an apparatus for imaging a body, such as an ultrasonic imaging system. In the disclosed apparatus, means are provided for transmitting energy, such as ultrasound energy, into the body. A transducer is provided for converting energy reflected from the body, typically ultrasound echoes, into electrical signals. The transducer, which is divided into a plurality of defined segments, such as concentric annular segments surrounding a central circular segment, is utilized for both transmitting and receiving. A plurality of register devices are provided, preferably analog registers of the charge-transfer type. The input of each of the register devices is coupled to a respective one of the transducer segments. A first clock is associated with each of the register devices. A plurality of second clocks are also provided, each being associated with one of the plurality of register devices. The second clocks have different characteristic clock rates. Timing means are provided for effecting clocking of the electrical signals from the segments into their respective devices with one of the device's associated clocks (i.e., either the common first clock or the device's associated second clock) and for subsequently effecting the clocking of the stored information out of each of the devices with the other of its associated clocks. Finally, means are provided for combining the signals clocked out of the devices to form an image-representative signal. In the present disclosure, the increasing or decreasing delay associated with the different transducer elements, as is required for dynamic focusing, is achieved by utilizing signals of slightly differing frequencies (e.g. the second clocks) so that, as time passes, the cumulative difference in sampling times for the different registers "builds up" to provide the desired variable delay.

29 Claims, 10 Drawing Figures

DYNAMIC FOCUSING APPARATUS AND METHOD

BACKGROUND OF THE INVENTION

This invention relates to apparatus for imaging a body and, more particularly, to an apparatus and method which employs an improved technique of dynamic focusing. The technique is particularly applicable to ultrasonic imaging systems.

During the past two decades ultrasonic techniques have become more prevalent in clinical diagnosis. Such techniques have been utilized for some time in the field of obstetrics, neurology and cardiology, and are becoming increasingly important in the visualization of subcutaneous blood vessels including imaging of smaller blood vessels.

Various fundamental factors have given rise to the increased use of ultrasonic techniques. Ultrasound differs from other forms of radiation in its interaction with living systems in that it has the nature of a mechanical wave. Accordingly, information is available from its use which is of a different nature than that obtained by other methods and it is found to be complementary to other diagnostic methods, such as those employing X-rays. Also, the risk of tissue damage using ultrasound appears to be much less than the apparent risk associated with ionizing radiations such as X-rays.

The majority of diagnostic techniques using ultrasound are based on the pulse-echo method wherein pulses of ultrasonic energy are periodically generated by a suitable piezoelectric transducer such as a lead zirconate-titanate ceramic. Each short pulse of ultrasonic energy is focused to a narrow beam which is transmitted into the patient's body wherein it eventually encounters interfaces between various different structures of the body. When there is a characteristic impedance mismatch at an interface, a portion of the ultrasonic energy is reflected at the boundary back toward the transducer. After generation of the pulse, the transducer operates in a "listening" mode wherein it converts received reflected energy or "echoes" from the body back into electrical signals. The time of arrival of these echoes depends on the ranges of the interfaces encountered and the propagation velocity of the ultrasound. Also, the amplitude of the echo is indicative of the reflection properties of the interface and, accordingly, of the nature of the characteristic structures forming the interface.

There are various ways in which the information in the received echoes can be usefully presented. In one common technique, the electrical signals representative of detected echoes are amplified and applied to the vertical deflection plates of a cathode ray display. The output of a time-base generator is applied to the horizontal deflection plates. Continuous repetition of the pulse/echo process in synchronism with the time-based signals produces a continuous display, called an "A-scan," in which time is proportional to range, and deflections in the vertical direction represent the presence of interfaces. The height of these vertical deflections is representative of echo strength.

Another common form of display is the so-called "B-scan" wherein the echo information is of a form more similar to conventional television display; i.e., the received echo signals are utilized to modulate the brightness of the display at each point scanned. This type of display is found especially useful when the ultrasonic energy is scanned transverse the body so that individual "ranging" information yields individual scanlines on the display, and successive transverse positions are utilized to obtain successive scanlines on the display. This type of technique yields a cross-sectional picture in the plane of the scan, and the resultant display can be viewed directly or recorded photographically or on magnetic tape. The transverse scan of the beam may be achieved by a reflector which is scanned mechanically over a desired angle.

In systems of the type described, the transducer is of finite size, and the beam transmitted and/or received by the transducer has a finite cross section which is a limiting factor on the resolution capabilities of the imaging system. It is known that the ultrasound beam can be "focused," by providing a suitable lens, such as is described in the U.S. Pat. No. 3,958,559, and/or by segmenting the transducer and coupling the different transducer segments to the transmitter/receiver circuitry via different delays. One can readily visualize the focusing effect of the segmented transducer in conjunction with different delays by observing that the ultrasound path to or from a given focal point to each of a plurality of concentric transducer segments is different for each segment. Typically, the geometrical path between the center transducer segment and the focal point is shortest and the geometrical path between the focal point and the outer transducer segment is longest, with the path to each intermediate transducer segment depending upon its size and relative position in the order of segments. Accordingly, ultrasound energy transmitted from the center segment would generally arrive at the focal point before the beam energy transmitted from the outer transducer segments and, similarly, an ultrasound echo reflected from the focal point will return sooner to the center transducer segment than to the outer transducer segments. Focusing is thus generally achieved by providing appropriately longer delays (typically, but not necessarily, electronic delays) in conjunction with the central segments of the transducer than are provided for the outer segments thereof.

It is also presently known in the art that the required delays vary as the focal point under consideration varies, as would typically be the case in a pulse echo system wherein information is to be received over a range of depths in the body being investigated by the ultrasound beam. In such instance, it is recognized that using fixed delays the beam is only "focused" at one particular focal length (or depth range), and the different geometries associated with other depths in the body require other delays to achieve an optimum focus at each point. Briefly, this can be visualized by recognizing that as the focal point moves deeper into the body, the difference between arrival times at the various transducer segments becomes less and less. Accordingly, a "dynamic focus" can be achieved (during receiving) by dynamically varying the delays associated with the different transducer segments such that the relative delays added to the more central transducer segments decrease as the focal point moves deeper into the body. Unfortunately, the need to provide a relatively large number of variable delays and circuitry to control these delays renders dynamic focusing an impractical expedient in many applications. The circuitry required therefor typically suffers one or more of the disadvantages of undue size, expense, complexity, and unreliability.

It is one object of the present invention to provide an imaging system and method including a dynamic focusing technique which overcomes disadvantage present in the prior art.

SUMMARY OF THE INVENTION

The present invention is directed to an apparatus for imaging a body, the invention being particularly applicable to an ultrasonic imaging system. In accordance with the invention, means are provided for transmitting energy, such as ultrasound energy, into the body. A transducer is provided for converting energy reflected from the body, typically ultrasound echoes, into electrical signals. The transducer, which is divided into a plurality of defined segments, such as concentric annular segments surrounding a central circular segment, is typically, although not necessarily, utilized for both transmitting and receiving. A plurality of register devices are provided, preferably analog registers of the charge-transfer type, such as charge-coupled device ("CCD") registers. The input of each of the register devices is coupled to a respective one of the transducer segments. A first clock is associated with each of the register devices. A plurality of second clocks are also provided, each being associated with one of the plurality of register devices. The second clock have different characteristic clock rates. Timing means are provided for effecting clocking of the electrical signals from the segments into their respective devices with one of the device's associated clocks (i.e., either the common first clock or the device's associated second clock) and for subsequently effecting the clocking of the stored information out of each of the devices with the other of its associated clocks. Finally, means are provided for combining the signals clocked out of the devices to form an image-representative signal.

In the present invention, the increasing or decreasing delay associated with the different transducer elements, as is required for dynamic focusing, is achieved by utilizing signals of slightly differing frequencies (e.g. the second clocks) so that, as time passes, the cumulative difference in sampling times for the different registers "builds up" to provide the desired variable delay. As will be described hereinafter, one embodiment of the invention utilizes the second clocks (which are of differing frequencies) to clock information into registers and the common clock (the same for each register device) to clock the stored information out. Another embodiment of the invention operates in the opposite manner with the first clock effecting the clocking in of information and the second clocks being utilized to clock information out. In a further embodiment of the invention, different clock frequencies are employed during both clocking in and clocking out.

Further features and advantages of the invention will become more readily apparent from the following detailed description when taken in conjunction with the accompanying drawings.

DESCRIPTION OF THE PREFERRED EMBODIMENT

Figure 1:
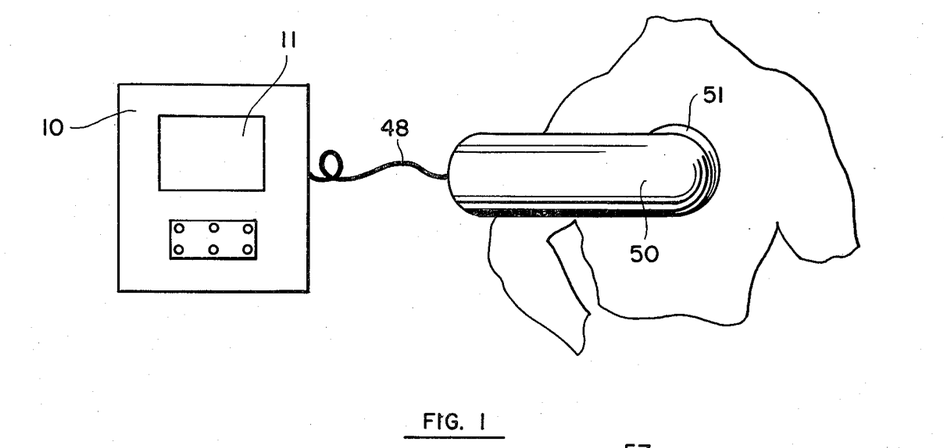
FIG. 1 illustrates the operation of an imaging apparatus which employs the improvements of the invention.

Referring to FIG. 1, there is shown an illustration of a scanning apparatus which employs the improvements of the invention. A console 10 is provided with a display 11 which may typically be a cathode ray tube television-type display, and a suitable control panel. A video tape recorder or suitable photographic means may also be included in the console to effect ultimate display of images. The console will typically house power supplies and portions of the timing and processing circuitry of the system to be described. A portable scanning module or probe 50 is coupled to the console by a cable 48. In the present embodiment the probe is generally cylindrical in shape and has a scanning window 51 near one end, the scanning window being defined by protruding flexible material, which may typically be silicone rubber. During operation of the apparatus, the probe 50 is hand-held to position the scanning window over a part of the body to be imaged. For example, in FIG. 1 the probe is positioned such that a cross section of the heart will be obtained. Imaging of other portions of the body is readily attained by moving the probe to the desired position and orientation, the relative orientation of the scanning window determining the angle of the cross section taken.

Figure 2:
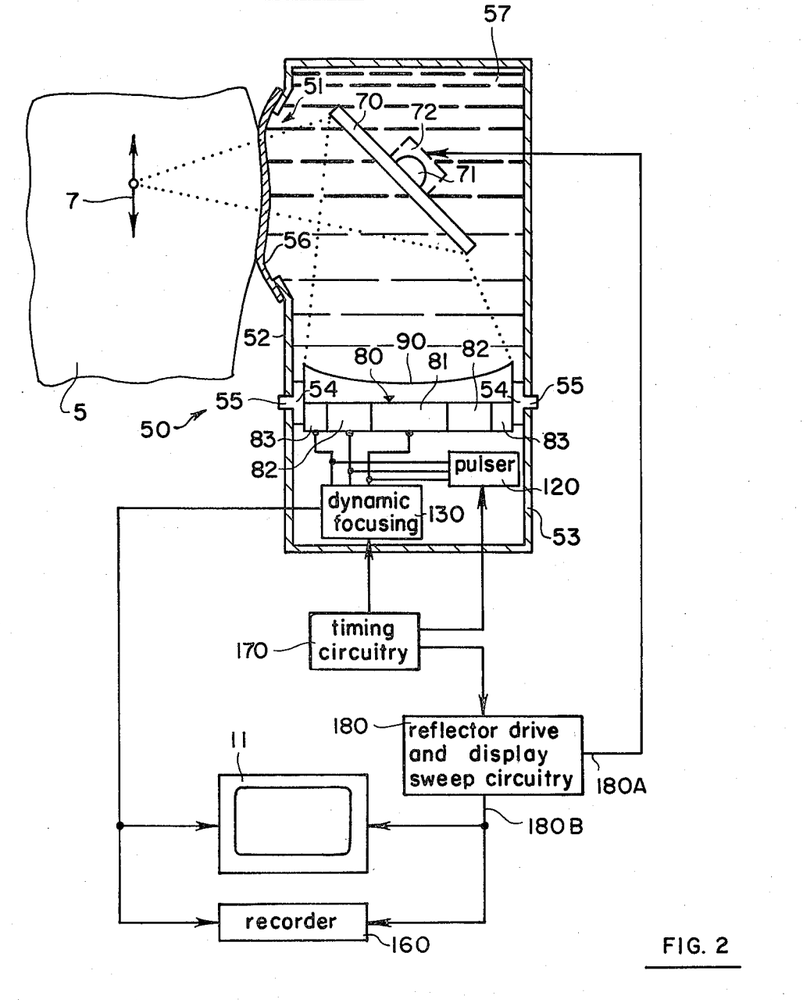
FIG. 2 is a schematic diagram, partially in block form, of an apparatus which employs the improvements of the invention.

Referring to FIG. 2, there is shown a cross-sectional view of a portion of the scanning module or probe 50 along with diagrams of portions of the circuitry therein and in console 10 used in conjunction therewith. An enclosure, which may be formed of plastic, consists of a front cover 52 which defines a fluid-tight compartment, and a rear cover 53 which houses at least a portion of the system electronics. Both covers are generally cylindrical in shape and fit, with suitable seals, over a cylindrical inner housing 54 having an annular rim 55. The inner housing holds a transducer 80 and a focusing lens 90, which may be in accordance with the description set forth in the U.S. Pat. No. 3,958,559. The scanning window 51 is defined by a generally rectangular opening in the side of cover 52, the opening having a slightly protruding lip on which is mounted a flexible material 56, which may be a silicone rubber membrane. The volume of the enclosure defined by front cover 52 is filled with a fluid 57, for example, water. The membrane 56 will accordingly conform in shape to the surface of a body portion with which it is placed in contact, thereby minimizing the possibility of an undesirable reflective liquid-air interface.

A reflective scanner 70, which is flat in the present embodiment but which may be curved to provide a degree of focusing if desired, is disposed in the fluid 57 between the lens 90 and the scanning window 51. The scanner 70 is mounted on a shaft 71 (perpendicular to the plane of the paper) which passes through a suitable seal in cover 52 and is connected to a small motor 72 which is mounted on the outside of cover 52 and provides the desired oscillatory motion.

The transducer 80 is divided into a plurality of segments, typically a central circular segment surrounded by concentric annular segments. In the present illustrations, only three segments designated 81, 82 and 83 are shown for ease of explanation, although it will be understood that a greater number of segments are typically employed, and the principles of the invention are readily applicable regardless of the number of segments employed. The transducer segments 81-83 are coupled to pulser circuitry 120 which provides energizing pulses to the transducer 80 in known manner. The transducer segments are also coupled to novel dynamic focusing circuitry in accordance with the invention. The circuit 130 is preferably operable during the receiving mode and processes the received echoes in a manner to be described. Suitable preamplification and amplification (not shown) can also be provided in the receiver portion of the circuitry. The output of dynamic focusing circuitry 130 is coupled to display 11 and recorder 160, which may be any suitable recording or memory means such as a video tape recorder. If desired, gain control circuitry may be provided and may include interactive gain compensation, which is described in detail in copending U.S. application Ser. No. 569,185, assigned to the same assignee as the present application. Interactive gain compensation circuitry compensates the amplitude of later arriving signals for attenuation experienced during passage through body tissue and losses due to prior reflections. Timing circuitry 170 generates timing signals which synchronize operation of the system; the timing signals being coupled to the circuitry 120 and 130 to alternately energize the transmitting and receiving modes, and also to reflector drive and display sweep circuitry 180, which generates the signals that control the oscillation of scanner 70 and the vertical and horizontal sweep signal for the display 11 and recorder 160.

In broad terms, operation of the system is as follows: Upon command from a trigger signal from the timing circuitry 170, the pulser 120 generates pulses which excite the segments of transducer 80. As is known in the art, the pulses can be relatively delayed so as to effect focusing of the ultrasound beam, and further focusing is provided by the lens 90. The ultrasound energy is reflected off the surface of scanner 70 and into the body 5, as represented in FIG. 2, the dashed light depicting the beam outline. When the ultrasound beam has been transmitted toward the body, the timing circuitry initiates the "receive" or "listen" mode by enabling the circuitry 130. Now, the transducer 80 serves to convert ultrasound energy, which is in the form of echoes reflected from the body and back off the scanner 70, into electrical signals. These signals are coupled, after processing by the circuitry 130, to the display 11. For a "B-scan" display, a sweep over a range of depths (which naturally results from the transmitted energy reflecting off different interfaces at successive depths in the body) corresponds to a horizontal scan line of the display. The second dimension of the desired cross-sectional image is obtained by a slower mechanical scan of scanner 70, the mechanical scanning range being illustrated by the double-headed arrow 7. Operation as described in this paragraph is generally in accordance with known techniques, the novel aspects of the present invention residing in the dynamic focusing circuitry 130 to be described.

Figure 3:
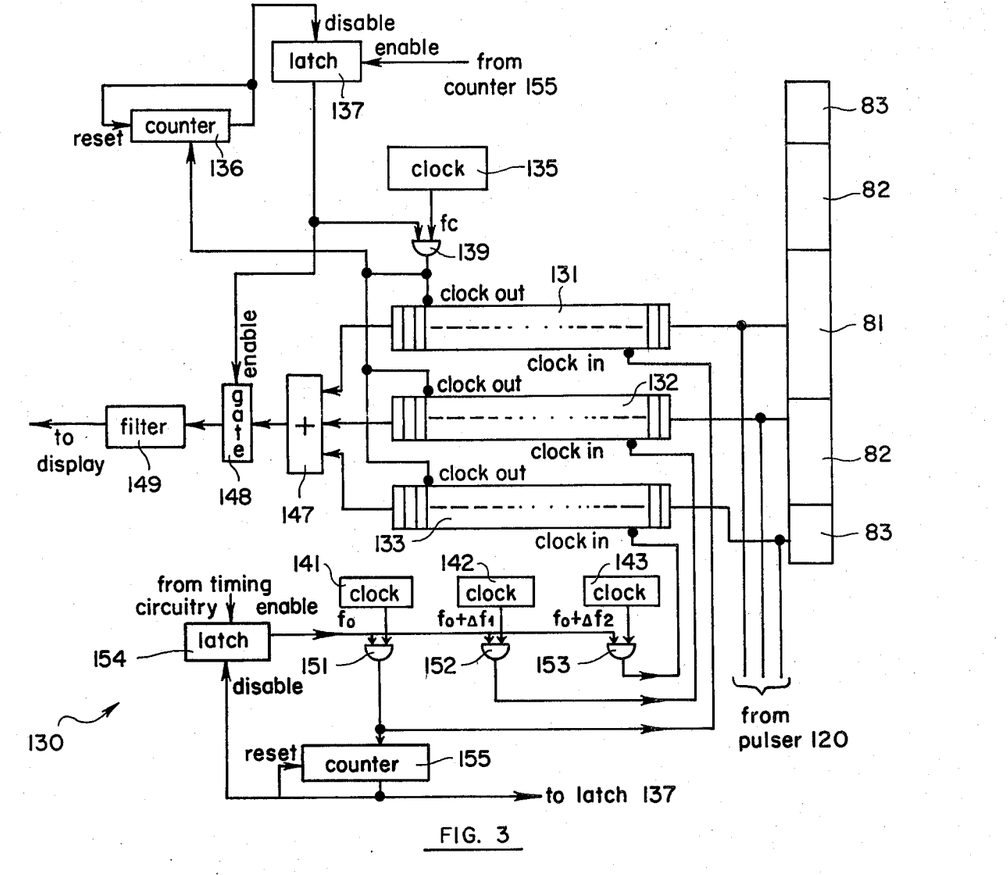
FIG. 3 is a schematic diagram, partially in block form, which illustrates an embodiment of the dynamic focusing circuitry in accordance with the invention.

Referring to FIG. 3, there is shown a block diagram of an embodiment of the dynamic focusing circuitry 130 coupled to the segments of transducer 80. A plurality of registers 131, 132 and 133 are respectively coupled to the transducer segments 81, 82 and 83. The registers are preferably analog registers of the charge transfer type, such as charge-coupled device ("CCD") registers. The output of the registers are coupled to an adder 147 whose output is, in turn, one input to a gate 148. The output of gate 148 is coupled, via a filter 149 which removes the clocking frequencies from the output, to the display 11. A plurality of clocks 141, 142 and 143 provide clock pulses which are utilized to clock information, from the transducer segments 81-83 into their respective registers 131-133. The clock 141 operates at a characteristic clock rate or frequency $f_o$, the clock 142 operates at a frequency $f_o + \Delta f_1$, and the clock 143 operates at a frequency $f_o + \Delta f_2$. The outputs of the clocks 141-143 are coupled to their respective registers via AND gate 151, 152 and 153 which serve to enable the "clock in" function. The other input to each of the AND gates 151-153 is the output of a latch 154. The output of AND gate 151, in addition to being coupled to register 131, is also coupled to a counter 155 which counts clock pulses at the clock rate $f_o$. In the present embodiment each of the registers 131-133 has N stages, and the counter 155 is a count-to-N counter. The output of the counter 155 is operative to reset the counter to zero and also to disable latch 154 which is enabled by a signal from the timing circuitry, this signal being the one previously referred to which initiates the "receive" or "listen" mode of the system. The signal from the timing circuitry is selected to occur at a particular time after transmission, and will depend upon the expected range over which useful echoes are to be measured.

A clock 135, which generates clock pulses at a characteristic clock rate or frequency $f_c$, is coupled to each of the registers 131, 132 and 133 and effects clocking out of the information in the registers. The output of the clock 135 is coupled to the registers via a gate 139. The output of the gate 139 is also coupled to a count-to-M counter 136. The output of counter 136 resets the counter to zero and also disables a latch 137 which is enabled by the output of the counter 155. The output of latch 137 is coupled to AND gate 139 and also to gate 148.

Operation of the circuitry 130 is as follows: Upon issuance of a signal from the timing circuitry, the latch 154 is enabled and, in turn, it enables the gates 151-153. Electrical signals from the transducer segments 81, 82 and 83 are now clocked into the registers 131, 132 and 133, respectively at the characteristic clock rates of the clocks 141-143. Clocking in will continue for N clock pulses; i.e., until the register 131 (which is being clocked in at the slowest clock rate) is filled. During clocking in, clock pulses at the frequency $f_o$ were also being counted by the counter 155. Upon reaching a count of N, the counter 155 issues an output which resets itself, disables the latch 154, and enables the latch 137. With latch 154 disabled, the gates 151-153 are also disabled and clocking in is terminated, as is the feed of clock pulses to counter 155. Enabling of the latch 137 causes enablement of the gates 139 and 148 and thereby initiates readout of the information in registers 131, 132 and 133, whose outputs are summed by adder 147 and then coupled, via gate 148 and filter 149, to the display 11. The filter 149 serves to remove the sampling clock frequencies from the signals coupled to the dispaly. During clocking out, clock pulses from clock 135 are counted by the counter 136 until N stored samples of information have been read out (assuming, for the time being, that M is set equal to N) whereupon the counter 136 issues an output which resets itself and disables the latch 137 which, in turn, disables the gates 139 and 148.

To understand the dynamic focusing achieved by the described operation, it is helpful to visualize the nature of the N samples which are contained in the three registers at the end of the clocking-in portion of operation. The information samples in the first (rightmost in the FIG.s) stage of each register were clocked in at substantially the same time and therefore have no relative delay associated with each other. Examining samples in corresponding stages of the three registers, for later stages thereof reveals that the time difference (or "delay") between samples in corresponding stages of the three registers increases as later stages of the registers are considered. For example, consider the information in the last (leftmost) stage of each register at the end of the clock-in-portion of the operation. Each of these samples represents information which was clocked in N clock periods prior to the time that the information comes to rest in the final register stage. The clock periods are the inverse of the clock frequencies. Accordingly, since the clock period associated with clocking into register 132 is shorter than the clock period associated with clocking into register 131, the time difference (or "delay") as between the information which comes to rest in the last stage of these two registers is equal to $N(\Delta T_1)$, where $\Delta T_1$ is the difference in clock periods. In general for stage n, the associated time difference or "delay" will be $n(\Delta T_1)$. In the case of register 133, the relative time difference as related to a corresponding stage n of register 131 is $n(\Delta T_2)$, where $\Delta T_2$ is the difference in clock periods as between the clocks 141 and 143. Thus it is seen that an effective "variable delay" over particular time span (corresponding to distance range over which echoes are considered) is achieved in this embodiment by clocking information into registers at different frequencies and subsequently clocking the information out of the registers at the same frequency.

Figure 4A:
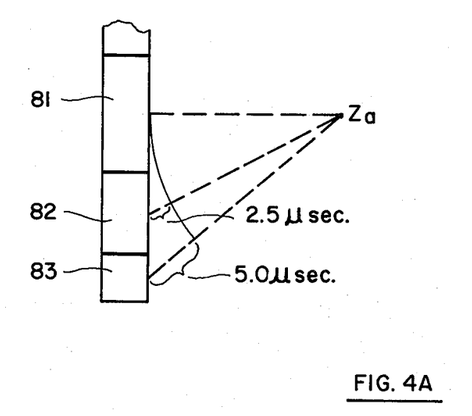
FIGS. 4A and 4B are useful in illustrating the functioning of the dynamic focusing circuitry in accordance with the embodiment of FIG. 3.
Figure 4B:
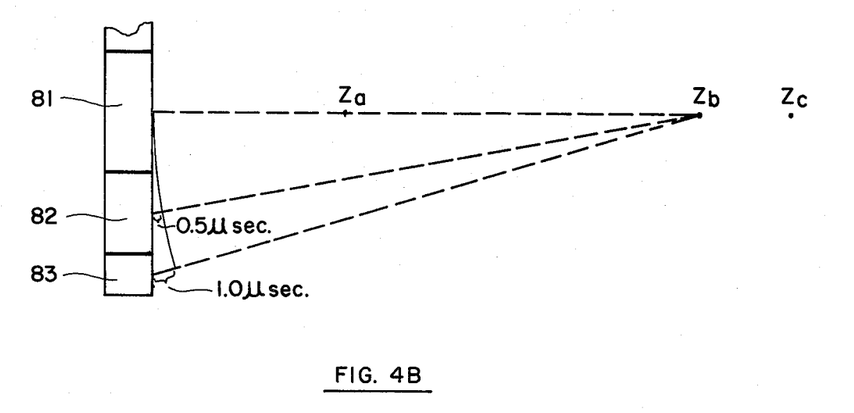

Referring to FIGS. 4A and 4B, there is shown a simplified example which illustrates the functioning of the dynamic focusing circuitry of FIG. 3. For this example, the focusing is described as being achieved without the need for fixed delay elements or a focusing lens, although it will be understood that these may typically, although not necessarily, be employed in conjunction with the invented technique. In FIG. 4A the point $z_a$ represents the nearest depth of investigation of the apparatus, and in FIG. 4B the point $z_b$ represents the furthest depth of investigation of the apparatus for purposes of this example. These points can presently be identified as theoretical foci, and it is convenient to identify the transducer segment 81 as the origin, so that distances to the two theoretical foci are $z_a$ and $z_b$, respectively. In FIGS. 4A and 4B, dashed lines represent the distances between each theoretical focus and the transducer segments 82 and 83. Portions of circles, having their centers at the theoretical foci and having respectively radii $z_a$ and $z_b$ are also shown in FIGS. 4A and 4B. For purposes of this example, the additional distances (beyond the circular portions) from the theoretical foci to each of the transducer segments are represented in the FIGS. in terms of propagation times through some particular propagation medium. For example, in FIG. 4A, for a particular propagation medium, an echo originating at the point $z_a$ would take about 2.5 microseconds longer to propagate to segment 82 than it would take to propagate to segment 81. Also, in this example, the propagation time to transducer segment 83 is about 5.0 microseconds longer than the propagation time to transducer segment 81. Similarly, in FIG. 4B, where the circular portion is seen to be of substantially larger radius, the "extra" distances are illustrated as being about 0.5 microseconds and 1.0 microseconds, respectively. Assume that N equals 1000, so that each of the registers 131-133 has 1,000 stages and the counter 155 counts to 1,000. Assume further that $f_o$ is 20 MHz, $\Delta f_1$ is 1.05 MHz, and $\Delta f_2$ is 2.22 MHz. Thus, the characteristic clock frequencies for clocks 141, 142 and 143 are respectively 20 MHz, 21.05 MHz and 22.22 MHz. Operation in accordance with this example is as follows: The timing circuitry is adjusted to issue the enable signal at about a time corresponding to the return of the earliest echo; i.e., the time at which an echo from the point $z_a$ is received at the transducer segment 81. Clocking into the registers 131-133 is now enabled and will continue for 50 microseconds, which corresponds to 1,000 clock pulses at the 20 MHz rate at which the counter 155 is counting. When the registers are full, the last stage of register 131 will contain echo information from the point $z_a$. The clock periods of the clocks 142 and 143 are 0.475 microseconds and 0.045 microseconds, respectively. Accordingly, at the end of the clocking-in period, the information in the last stage of the register 132 will be information which was clocked into the first stage of register 132 1,000 clock periods ago; i.e., 47.5 microseconds ago (1,000 multiplied by 0.0475 microseconds). Similarly, the information in the last stage of the register 133 will be information which was clocked into the first stage of register 133 45 microseconds ago (1,000 multiplied by 0.045 microseconds). Thus it is seen that the echo information from point $z_a$ will be in the last stage of each register, the higher clock rates of the clocks 142 and 143 having "advanced" this information by times which correspond to the additional propagation times necessary for the echo from point $z_a$ to reach the transducer segments 82 and 83. Another way of stating this "compensation" is that the lower clock rates of clocks 142 and 141 effectively introduce the appropriate "delay" to compensate for differences in propagation time and thereby achieve an effective focus of the echo from point $z_a$. Examination of the information in other corresponding register stages reveals that the amount of relative delay decreases for lower numbered corresponding stages of the registers. (Bearing in mind that since the registers are all clocked out at the same clock rate in this embodiment, information in corresponding stages will be clocked out together and thus added together.) In general, the relative time reference for information in corresponding register stages depends upon the stage number (which determines how many clock pulses were needed to get information to the particular stage) and the characteristic clock period of each register's clock.

Consider, now, the situation of FIG. 4B wherein an echo is returned from the point $z_b$. In this example, it is assumed that the point $z_b$ is about 40 microseconds propagation time further away from the origin than the point $z_a$ and that the differences in propagation time to the transducer segments 82 and 83 have shrunk to 0.5 microseconds and 1.0 microseconds, respectively. Echo information from the point $z_b$ will arrive at the transducer segment 81 40 microseconds after arrival of echo information from the point $z_a$; that is 40 microseconds after initiation of clocking-in. Ten microseconds later, i.e., at the end of clocking-in, the echo information from the point $z_b$ will come to rest in the 200th stage of register 131. The information in the corresponding 200th stage of register 132 will be information that had been originally clocked into the first stage of register 132 9.5 microseconds before it came to rest in the 200th stage (200 clock pulses multiplied by the 0.0475 microsecond clock period). Similarly, the information which comes to rest in the 200th stage of register 133 will be information which had been originally clocked into register 133 9 microseconds before it came to rest in the 200th stage (200 clock pulses multiplied by the 0.045 microsecond clock period). Accordingly, it is seen that for the present example the information contained in the 200th stage of each of the registers represents echo information from the point $z_b$, the additional propagation time to transducer segments 82 and 83 having been "compensated" by the higher frequency clocks 142 and 143. The amount of relative delay is thus seen to decrease for further depths of investigation, thereby achieving the objectives of dynamic focusing. In the example of FIGS. 4A and 4B, dynamic focusing is seen to be achieved over the indicated range, and the need for additional fixed delays (during receiving) is obviated, over the range shown, by clocking out only the last 800 stages of the registers, as can be achieved by setting M for counter 136 equal to 800. It may be preferable, however, to employ appropriate fixed delays at the far focal point and have the variable delay introduced by the registers and clocks vary from the maximum value (e.g. for arrivals from point $z_a$) down to zero at some far focal point $z_c$. This can be visualized in the example of FIGS. 4A and 4B by assuming that the far focal point $z_c$ is further removed from the origin and is a total of 50 microseconds propagation time removed from the near focus $z_a$. In such case, the information in the full 1000 stages of the three registers would be clocked out and the relative delay as between the information which had originally come to rest in the first stage of the registers would have zero delay introduced by the system shown in FIG. 3. In such instance, appropriate fixed delays could be added to the lines coupled to transducer segments 82 and 83 to compensate for the difference in propagation time to the transducer segments from the point $z_c$ (and the delays introduced by the present system scaled down by amounts corresponding to the fixed delays).

Figure 5:
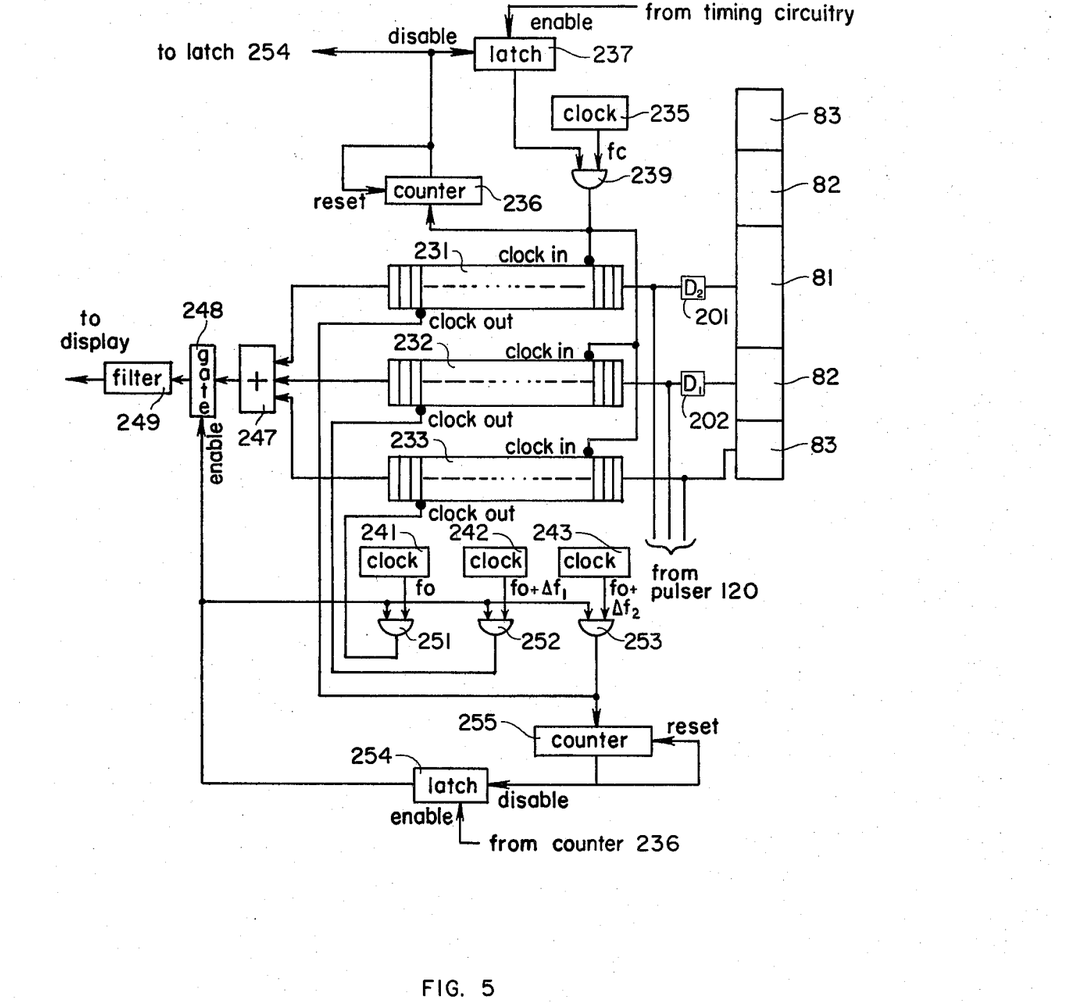
FIG. 5 is a schematic diagram partially in block form, which illustrates another embodiment of the dynamic focusing circuitry in accordance with the invention.

Referring to FIG. 5, there is shown an embodiment of the invention wherein information from the transducer segments is clocked into registers 231, 232 and 233 at the same frequency, $f_c$, under control of the clock 235, and are clocked out at different frequencies $f_o$, $f_o+\Delta f_1$ and $f_o+\Delta f_2$, under control of the clocks 241, 242 and 243, respectively. Count-to-N counter 236, latch 237, and AND gate 239 operate in the manner previously described to enable clocking in, upon receipt of a signal from the timing circuitry, for N clock pulses. Latch 254 is enabled by an output from counter 236 (which indicates the end of clocking-in) and initiates clocking out by enabling the AND gates 251, 252 and 253. Outputs of the registers 231–233 are added by adder 247 and then coupled, via gate 248 and filter 249, to the display 11. In the embodiment of FIG. 5, the transducer segments 82 and 81 are coupled to their respective registers via delays $D_1$ and $D_2$. Also, the highest frequency clock is, in this instance, used to clock out the register 231 which is coupled to the central transducer segment 81, and successively lower frequency clocks are utilized to clock out successively outer transducer segments. The counter 255, which limits the clocking out action by disabling the latch 254, is coupled to the highest frequency clock 243 so as to limit the clocking-out to N clock pulses.

Figure 6A:
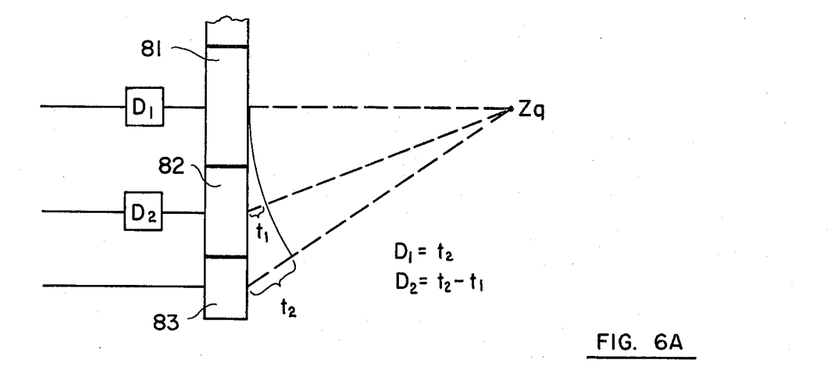
FIGS. 6A and 6B are useful in illustrating the functioning of the dynamic focusing circuitry in accordance with the embodiment of FIG. 5.
Figure 6B:
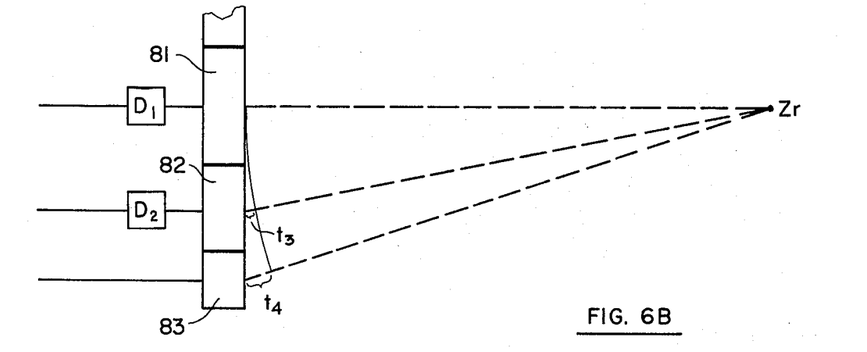

Operation of the embodiment of FIG. 5 is illustrated with the aid of FIGS. 6A and 6B. FIG. 6A illustrates the geometry associated with a near focus, designated $z_q$. The additional echo transit time from point $z_q$ to the segments 82 and 83, as compared to the transit time to central segment 81, are $t_1$ and $t_2$, respectively. Accordingly, by providing fixed delays $D_1=t_2$ and $D_2=t_2-t_1$, focusing at the point $z_q$ is achieved. The enable signal from the timing circuitry (which enables latch 237) is adjusted to coincide with arrival of the echo from point $z_q$ at the transducer segment 83 (and will also correspond in time to the arrival of an echo from this point at the input to the registers 231 and 232, due to the delays $D_2$ and $D_1$). N clock pulses of information will now be clocked into the three registers at the same frequency, $f_c$, and the echo information from the point $z_q$ will come to rest in about the last stages of the registers 231–233. Assume that the frequency $f_c$ is selected such that the information which comes to rest in the first stage of register 231 is from the point designated $z_r$ in FIG. 6B. Geometrically, it is seen that delay times determined from propagation times designated $t_3$ and $t_4$ (i.e., a new $D_1^*=t_4$ and a new $D_2^*=t_4-t_3$) would be needed. Thus, the fixed delays $D_1$ and $D_2$ are too large. In the present embodiment the signals from the central segments are effectively "advanced" by increasing amounts as the focal point moves outward, this being achieved by clocking out the registers 232 and 231 at successively higher frequencies. The concept is similar to that described in conjunction with FIG. 3, except it is reversed. In particular, the information which had come to rest in the last stages of the respective registers 231–233 will experience no relative "delay" due to the clocking out operation since they are the initial samples of information clocked out and the difference in clock-out frequencies will not introduce any appreciable delay. In contrast, the last samples of information to be clocked out will experience the maximum relative delay, with the delay varying for the in-between samples, as is desirable for dynamic focusing. The clock frequencies are selected such that the information clocked out of register 231 is "advanced" with respect to the information clocked out of register 233 by a time $t_2-t_4$, and the information clocked out of register 232 is "advanced" with respect to information clocked out of register 233 by a time $t_1-t_3$. This may be achieved by selecting $N(\Delta T_1)=t_1-t_3$ and $N(\Delta T_2)=t_2-t_4$, where $\Delta T_1$ and $\Delta T_2$ are the differences in clock periods of the clocks 242 and 243 as compared to the clock 241. It should be noted that in the present embodiment less than the full number of stages of the registers 232 and 233 will be clocked out since N clock pulses at the highest clock rate (at which register 231 is clocked out) fully empties the register 231.

Figure 7:
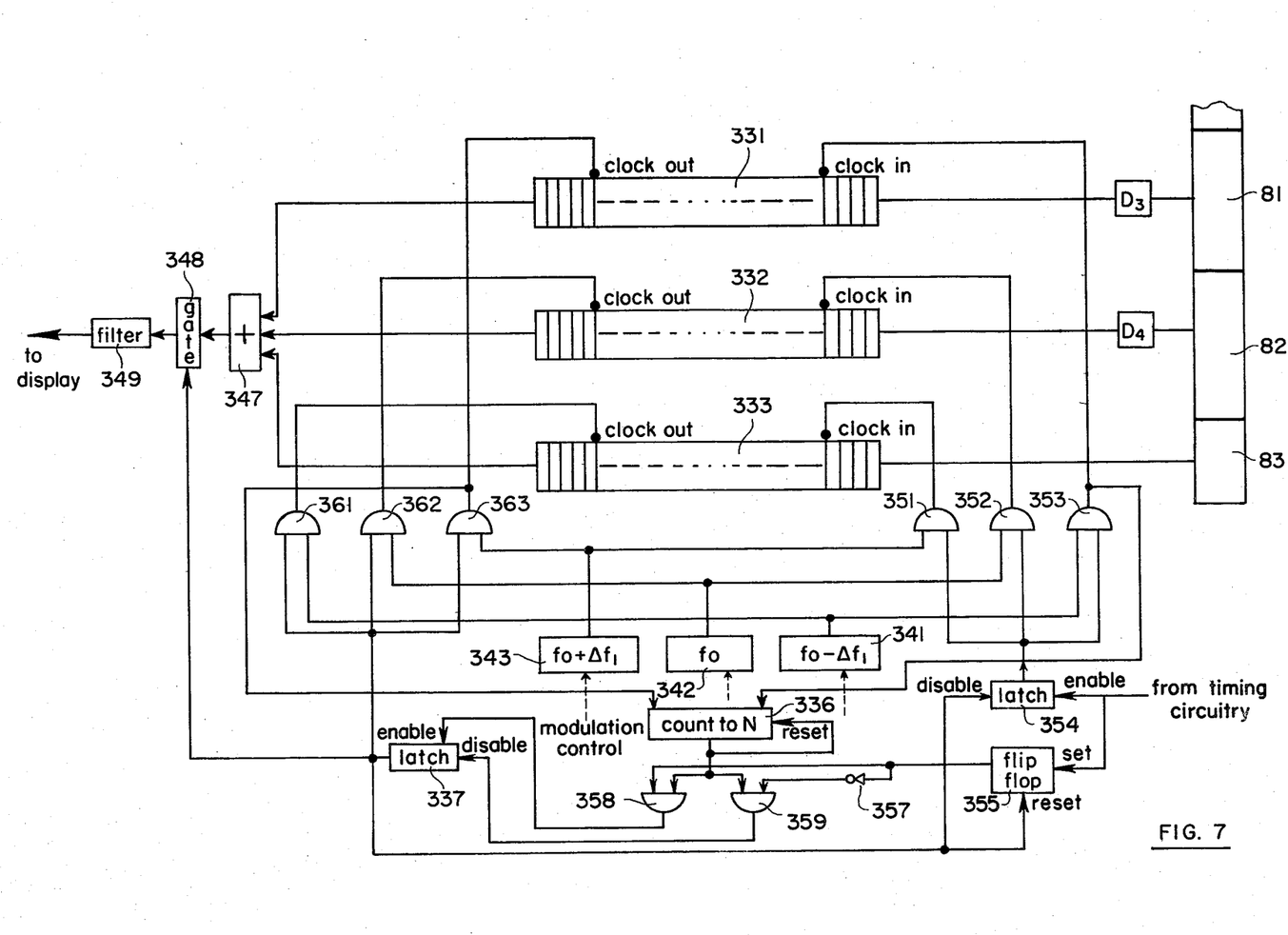
FIG. 7 is a schematic diagram, partially in block form, which illustrates a further embodiment of the dynamic focusing circuitry in accordance with the invention.
Figure 8:
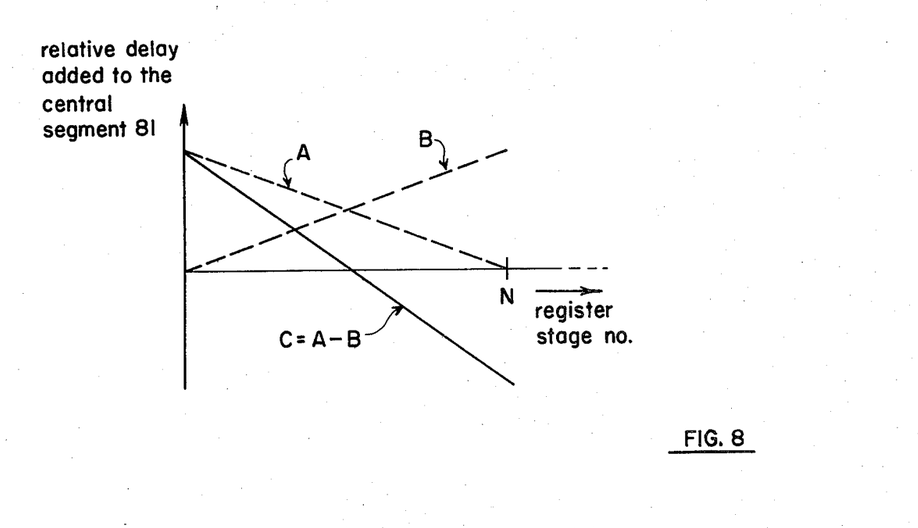
FIG. 8 is a graph which is useful in understanding the functioning of the dynamic focusing circuitry of FIG. 7.

Referring to FIG. 7, there is shown a further embodiment of the invention wherein the information from the transducer segments are clocked into respective registers at different clock frequencies and subsequently clocked out of the registers at different clock frequencies. During clocking in, the clock frequencies associated with transducer segments in a particular order are of increasing frequency while during the clocking out operation, the registers associated with the transducer segments over the particular order thereof are of decreasing frequency. In particular, registers 331, 332 and 333 are respectively coupled to transducer segments 81, 82 and 83, the segments 81 and 82 being coupled to their respective registers via delays designated $D_3$ and $D_4$ so as to provide a fixed-delay focal point which, as will be described, is a point that is generally central in the range of dynamic focusing of this embodiment. Clocks 341, 342 and 343, of ascending frequencies designated as $f_0 - \Delta f_1$, $f_0$, and $f_0 + \Delta f_1$, are provided. During clocking-in, clocks 341–343 are coupled to registers 331–333 via the AND gates 351, 352 and 353, respectively, which are enabled by the output of a latch 354. During clocking-out, the clocks 341–343 are coupled to the registers in reverse order via the AND gates 361, 362 and 363, respectively, the AND gates being enabled by the output of a latch 337. The outputs of the registers are summed by adder 347 and coupled via gate 348 and filter 349 to the display 11. The gate 348 is enabled by the output of latch 337 during clocking-out. In this embodiment a single count-to-N counter 336 is used to keep track of both the clocking-in and clocking-out operations. Upon the initial signal from the timing circuitry, the latch 354 is enabled and thereby enables the gates 351–353 to allow clocking-in. At the same time a flip-flop 355 is set. The output of the flip-flop 355 is used to keep track of whether the clocking-in or clocking-out portion of operation is active. During clocking-in, the output of the flip flop 355 is "high" and enables an AND gate 358. During clocking-in the count-to-N counter 336 counts clock pulses from the lowest frequency clock (341) until a count of N is reached whereupon the counter 336 issues an output (and also resets itself). With the AND gate 358 enabled, the output of counter 336 enables latch 337 which, in turn, enables clocking-out by enabling AND gates 361–363 and gate 348, and also disables the latch 354 (to terminate clocking-in) and resets the flip-flop 355. The output of flip-flop 355 will now be "low", but it is inverted by inverter 357 so as to enable the AND gate 359. During clocking-out, the counter 336 counts clock pulses of the highest frequency clock (343) until a count of N is reached whereupon the counter 336 generates an output which resets itself and also, via enabled AND gate 359, disables latch 337 to terminate clocking-out. In the embodiment of FIG. 7, both of the types of delay described in conjunction with FIGS. 3 and 5 are employed on opposite sides of the central focus. During clocking-in, delay is successively added to the more central transducer segments since they are clocked in at the lower frequencies, so that, for example, the information samples which come to rest in the last stages of the respective registers have a maximum relative delay imparted to them by the dynamic focusing system. The relative delay due to clocking-in successively decreases for earlier stages (similar to FIG. 3 situation) as illustrated by the dashed line "A" in the graph of FIG. 8. During clocking out, the reverse situation is true (similar to the FIG. 5) as illustrated by the dashed line "B" in FIG. 8. The cumulative delay due to the dynamic focusing system is represented by the line C (equal to A-B) in FIG. 8. Relative delay is zero at about the center of the register (corresponding to about the center of the range), and appropriate fixed delays can be utilized at this point.

In the embodiments set forth, a simplifying assumption is made that the variation in delay required for the different transducer segments (as a function of time—i.e. as the theoretical focal point moves outward) is proportional to focal length. While this is not precisely true, the dynamic focusing provided is a linear approximation of the exact delays required for theoretically perfect dynamic focusing. In the embodiments of FIGS. 3 and 5 the precise required delay can be selected, for example, at the two "end" focal points, whereas in the embodiment of FIG. 7 the precise required delays can be selected at the "end" focal points and also at the central focus wherein delay introduced by clocking frequency difference is zero. A desired waveform for delay versus time, other than a linear approximation, can be achieved by frequency modulating the clocks during the clocking in and/or clocking out operations. This may be achieved, for example, by utilizing voltage controlled oscillators as the clocks and controlling the clocks with varying voltages having any particular desired waveform, as depicted generally in FIG. 7 by the dashed arrow inputs to the clocks 341–343. The modulation will preferably cause the clocking frequencies to converge or diverge during clocking in and/or clocking out.

The invention has been described with reference to particular embodiments, but variations within the spirit and scope of the invention will occur to those skilled in the art. For example, while registers having the same number of stages have been described, it will be understood that registers having different numbers of stages may be employed and the number of samples clocked into different registers can be counted. Also, it will be understood that in the embodiments of FIGS. 3 and 5 the common clock could be one of the clocks used during the other clocking function. Further, it will be understood that in the embodiment of FIG. 7 different physical clocks could be used for the clocking in and clocking out functions.

I claim:

1. Apparatus for imaging a body, comprising:
   means for transmitting energy into the body;
   a transducer for converting energy reflected from said body to electrical signals, said transducer being divided into a plurality of defined segments;
   a plurality of register devices, the input of each of said register devices being coupled to a respective one of said transducer segments;
   a first clock associated with each of said register devices;
   a plurality of second clocks, each associated with one of said plurality of register devices, each of said second clocks having a different characteristic clock rate;
   timing means for effecting clocking of said electrical signals from said segments into their respective devices with one of its associated clocks and for subsequently effecting the clocking of the stored information out of each of said devices with the other of its associated clocks; and
   means for combining the signals clocked out of said devices to form an image-representative signal.

2. Apparatus as defined by claim 1 wherein said energy is ultrasound energy.

3. Apparatus as defined by claim 2 wherein said timing means effects clocking into the respective devices with their associated second clocks and clocking out of said devices with said first clock.

4. Apparatus as defined by claim 3 wherein said register devices are analog registers of the charge-transfer type.

5. Apparatus as defined by claim 2 wherein said transducer segments comprise a central circular segment and concentric annular segments.

6. Apparatus as defined by claim 5 wherein said timing means effects clocking into the respective devices with said first clock and clocking out of said devices with their associated second clocks.

7. Apparatus as defined by claim 6 wherein the second clock associated with said circular segment has a higher characteristic clock rate than the second clocks associated with said annular segments.

8. Apparatus as defined by claim 7 wherein the second clocks associated with said annular transducer segments have increasingly lower characteristic clock rates associated with increasingly outer annular segments.

9. Apparatus as defined by claim 5 wherein the second clock associated with said circular segment has a lower characteristic clock rate than the second clocks associated with said annular segments.

10. Apparatus as defined by claim 9 wherein said timing means effects clocking into the respective devices with their associated second clocks and clocking out of said devices with said first clock.

11. Apparatus as defined by claim 9 wherein the second clocks associated with said annular transducer segments have increasingly higher characteristic clock rates associated with increasingly outer annular segments.

12. Apparatus as defined by claim 11 wherein said timing means effects clocking into the respective devices with their associated second clocks and clocking out of said devices with said first clock.

13. Apparatus as defined by claim 2 wherein said timing means effects clocking into the respective devices with said first clock and clocking out of said devices with their associated second clocks.

14. Apparatus as defined by claim 13 wherein said register devices are analog registers of the charge-transfer type.

15. Apparatus for imaging a body, comprising: means for transmitting energy into the body;
a transducer for converting echoes reflected from said body into electrical signals, said transducer being divided into a plurality of defined segments;
a plurality of register devices, the input of each of said register devices being coupled to a respective one of said transducer segments;
a plurality of clocks having different characteristic clock rates;
timing means for effecting clocking of said electrical signals from said segments into their respective devices at different clock rates by clocking in with different ones of said clocks with a particular order of association between said clocks and said devices and for subsequently effecting the clocking of the stored information out of said devices at different clock rates by clocking out with different ones of said clocks but with another order of association between said clocks and said devices; and
means for combining the signals clocked out of said devices to form an image-representative signal.

16. Apparatus as defined by claim 15 wherein the transmitted energy is ultrasound energy.

17. Apparatus as defined by claim 16 wherein the transducer segments comprise a substantially circular central segment and concentric annular segments surrounding the central segment.

18. Apparatus as defined by claim 17 wherein successively higher frequency clocks are utilized for clocking information into the devices associated with successively greater radius segments.

19. Apparatus as defined by claim 18 wherein successively lower frequency clocks are utilized to clock information out of the devices associated with transducer segments of successively greater radius.

20. Apparatus as defined by claim 15 wherein said register devices are analog registers of the charge-transfer type.

21. For use in conjunction with an apparatus for imaging a body by transmitting ultrasound energy into the body and then converting echoes reflected from the body to electrical signals using a transducer divided into a plurality of segments; an improved method for dynamic focusing, comprising the steps of;
providing a plurality of register devices, each associated with a respective one of the transducer segments;
clocking electrical signals from the transducer segments into their respective devices at a respectively different clock frequency for each segment;
clocking the stored information out of said devices at the same frequency; and
combining the information clocked out of said device to form an image-representative signal.

22. The method as defined by claim 21 wherein the step of clocking into said devices at different clock frequencies includes the step of modulating the clocking frequencies during clocking in.

23. For use in conjunction with an apparatus for imaging a body by transmitting ultrasound energy into the body and then converting echoes reflected from the body to electrical signals using a transducer divided into a plurality of segments; an improved method for dynamic focusing, comprising the steps of:
providing a plurality of register devices, each associated with a respective one of the transducer segments;
clocking electrical signals from the transducer segments into their respective devices at the same frequency;
clocking the stored information out of said devices at a respectively different clock frequency for each segment; and
combining the information clocked out of said devices to form an image-representative signal.

24. The method as defined by claim 23 wherein the step of clocking out of said devices at different clock frequencies includes the step of modulating the clocking frequencies during clocking out.

25. A method for imaging a body, comprising the steps of:
transmitting energy into the body;
converting echoes reflected from said body into electrical signals with a transducer that is divided into a plurality of defined segments;
providing a plurality of register devices, the input of each of said register devices being coupled to a respective one of said transducer segments;
effecting clocking of said electrical signals from said segments into their respective devices at different clock rates, with a particular order of association between said clock rates and said devices;

effecting clocking of the stored information out of said devices at different clock rates, but with another order of association between said clocks and said devices; and combining the signals clocked out of said devices to form an image-representative signal.

26. The method as defined by claim 25 wherein the transmitted energy is ultrasound energy.

27. The method ad defined by claim 26 wherein the transducer segments comprise a substantially circular central segment and concentric annular segments surrounding the central segment.

28. The method as defined by claim 27 wherein successively higher clock rates are utilized for clocking information into the devices associated with successively greater radius segments.

29. The method as defined by claim 28 wherein successively lower clock rates are utilized to clock information out of the devices associated with transducer segments of successively greater radius.

* * * * *